United States Patent [19]
Chan et al.

[11] 4,299,965
[45] Nov. 10, 1981

[54] PREPARATION OF BENZOTRIAZOLE

[75] Inventors: Marie S. Chan; Wood E. Hunter, both of Pittsburgh, Pa.

[73] Assignee: Calgon Corporation, Pittsburgh, Pa.

[21] Appl. No.: 164,453

[22] Filed: Jun. 30, 1980

[51] Int. Cl.$^3$ ............................................ C07D 249/18
[52] U.S. Cl. .................................................... 548/257
[58] Field of Search ........................................ 548/257

[56] References Cited

U.S. PATENT DOCUMENTS 2,861,078  11/1958  Miller et al. ........................ 548/257
3,227,726  1/1966   Levy .................................... 548/257
3,334,054  8/1967   Howard et al. ..................... 548/257
3,564,001  2/1971   Long ................................... 548/257

Primary Examiner—Paul M. Coughlan, Jr.
Attorney, Agent, or Firm—Mario A. Monaco; Martin L. Katz; R. Brent Olson

[57] ABSTRACT

Low temperature process for the preparation of benzotriazole at high solids concentrations by the reaction of orthophenylenediamine, sodium nitrite and acetic acid in an aqueous medium at a temperature in the range of from 5° to 25° C., and neutralizing with caustic to liberate benzotriazole in quantitative yield.

4 Claims, No Drawings

PREPARATION OF BENZOTRIAZOLE

This invention relates to an improved process for the preparation of 1,2,3-benzotriazole.

More particularly, this invention relates to an improved process for the preparation of 1,2,3-benzotriazole at high solids concentrations in which the entire reaction is carried out at low temperatures, and product liberation is aided by caustic neutralization.

1,2,3-benzotriazole is widely used as a copper corrosion inhibitor; as an intermediate in the preparation of dyes, fungicides and plant growth regulators; and as a polymerization catalyst.

The prior art discloses several processes for the preparation of 1,2,3-benzotriazole, involving diazotization. The method essentially comprises mixing a nitrite salt, orthophenylenediamine and an acid in an aqueous system and conducting the reaction entirely at a high temperature, above about 50° C., or initially at a low temperature of from about 0° C. to 50° C. and then at a higher temperature above about 50° C. These processes are disclosed in U.S. Pat. Nos. 2,861,078; 3,227,726; 3,334,054 and 3,564,001. The initial products formed by the above-described methods are crude and not of high quality. To obtain a high quality product, the benzotriazole thus formed must be further processed by carbon treatment, crystalization or distillation processing steps, which are both expensive and time-consuming. In addition, these methods for preparing benzotriazole generally have been conducted at low solids, resulting in concentrations of less than 15 percent benzotriazole in the final reaction mixture.

Accordingly, it is an object of the present invention to provide a process for the preparation of 1,2,3-benzotriazole which is relatively simple, quick and less energy-intensive than the prior art processes.

It is a further object of the present invention to provide a process for the preparation of 1,2,3-benzotriazole which can be run at high solids concentrations.

It is an additional object of the present invention to provide a process for the preparation of 1,2,3-benzotriazole which does not require hazardous or complex purification procedures to produce technical grade product.

These and other objects of the present invention are accomplished by a process for the preparation of 1,2,3-benzotriazole in which orthophenylenediamine, sodium nitrite and acetic acid are reacted at high solids concentrations in an aqueous medium at a temperature of from 5° C. to 25° C., and the reaction mixture is treated with caustic to liberate high yields of solid product. After filtration, the product is water-washed to produce a technical grade product.

In carrying out the process of the present invention, an aqueous mixture or orthophenylenediamine and acetic acid is slowly added to a cooled sodium nitrite solution and the reaction carried out for a period of one to three hours at a concentration of from about 12 to about 22 percent by weight concentration of active ingredients. The order of addition of reagents is not important, as long as one reagent is added to the other at a rate sufficient to keep the temperature of the reaction below about 25° C. The reaction is followed by neutralization of the reaction mixture to a pH of 6 to 6.5 with sodium hydroxide. The entire reaction and neutralization process is carried out at low temperature, between 5° C. and 25° C. A precipitate of 1,2,3-benzotriazole is formed, filtered and washed with cold water to yield technical grade product suitable for use in industrial applications.

In carrying out the process of the present invention, concentrations of reactants in water are adjusted to give 15 to 25 percent by weight of product benzotriazole, mole ratios of 0.9 to 1.1 for orthophenylenediamine to sodium nitrite and 1.8 to 2.2 for acetic acid to orthophenylenediamine are required. Levels of caustic for neutralization must be less than 0.8 moles per mole acetic acid.

The process of the present invention may be illustrated by the following representative examples.

EXAMPLE 1

In a 1 liter resin kettle, 56 g of sodium nitrite was dissolved in 100 g of water. The mixture was cooled to ice temperature over an ice bath. A mixture of 81.0 g of orthophenylenediamine, 90 g of glacial acetic acid, and 200 g of water was pumped into the cooled nitrite solution over a period of two hours. The temperature of the mixture was maintained below 15° C. A yellow precipitate was formed. After addition of the reagents was complete, the mixture was stirred and cooled for an additional 10 to 15 minutes. The mixture was filtered through a Buchner funnel over a vacuum. The filter cake was washed with three portions of 100 ml ice water. The filter cake was sucked dry over the vacuum and then dried in a vacuum oven. The dried product represents an 81 percent yield and the melting point of the product is 93° C. Active benzotriazole was found to be 93 percent by potentiometric titration.

EXAMPLE 2

The procedure of Example 1 was repeated until the completion of adding the amine/acid/water mixture. Stirring continued for an additional 10 to 15 minutes. Then, 50 percent aqueous sodium hydroxide, made from 30 g of sodium hydroxide flakes, was added to the mixture over 20 minutes. The temperature during this neutralization step was kept below 10° C. The neutralized mixture was then filtered, washed and dried in the same manner as in Example 1. The product represents a 99 percent yield. Melting point is 93° C. Active bonzotriazole is 91 percent.

EXAMPLE 3

The procedure of Example 1 was repeated, except that the nitrite was dissolved in 80 g water, instead of 100 g. The amine/acid mixture was diluted with 100 g of water, instead of 200 g. The product has a melting point of 92° C. and 90 percent active benzotriazole. Ninety-two percent yield was achieved.

EXAMPLE 4

The procedure of Example 3 was repeated and the neutralization step was carried out in the same manner as in Example 2. The product has a melting point of 94° C. and 92 percent active benzotriazole. A 100 percent yield was achieved.

We claim:

1. A process for the preparation of 1,2,3-benzotriazole which comprises continuously adding an aqueous solution of acetic acid and orthophenylenediamine to an aqueous solution of sodium nitrite over a period of from 1 to 3 hours at a temperature between 5° C. and 25° C. until the reaction is substantially complete and, thereafter, separating the 1,2,3-benzotriazole from the reaction mixture.

2. The process of claim 1 which comprises the use of continuous addition of reagents in an amount to obtain an overall 1,2,3-benzotriazole concentration of 15 to 25 percent by weight.

3. The process of claim 1 which comprises the additional step of neutralizing the reaction mixture to a pH of 6 to 6.5 with sodium hydroxide.

4. The method of claim 1 wherein the 1,2,3-benzotriazole is recovered directly from the reaction mixture in solid form.

* * * * *